United States Patent

Saettone et al.

(10) Patent No.: US 6,423,307 B2
(45) Date of Patent: *Jul. 23, 2002

(54) BIOADHESIVE COMPLEXES OF POLYCARBOPHIL AND AZOLE ANTIFUNGAL OR ANTIPROTOZOAL DRUGS

(75) Inventors: Marco Fabrizio Saettone; Luana Panichi; Boris Giannaccini; Enrico Boldrini; Pietro Bianchini, all of Pisa (IT)

(73) Assignee: Farmigea S.p.A., Pisa (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/230,863
(22) PCT Filed: Jul. 25, 1997
(86) PCT No.: PCT/IT97/00187
§ 371 (c)(1), (2), (4) Date: Feb. 2, 1999
(87) PCT Pub. No.: WO98/05303
PCT Pub. Date: Feb. 12, 1998

(30) Foreign Application Priority Data

Aug. 2, 1996 (IT) ........................ RM96A0559

(51) Int. Cl.[7] .................... A61K 31/74; A61K 9/00; A01N 25/00; A01N 25/24
(52) U.S. Cl. .................... 424/78.18; 424/400; 424/405; 424/407; 514/772.2
(58) Field of Search .................... 424/78.18, 426, 424/400, 407, 405; 514/724, 772.2; 609/890

(56) References Cited

U.S. PATENT DOCUMENTS

| 4,615,697 A | * | 10/1986 | Robinson ..................... 604/890 |
| 5,658,956 A | * | 8/1997 | Martin et al. ................ 514/724 |
| 6,156,348 A | * | 12/2000 | Santos et al. ................ 424/426 |

FOREIGN PATENT DOCUMENTS

| EP | 0501523 A1 | 2/1992 |
| EP | 0497956 B1 | 1/1996 |
| EP | 0770384 A1 | 2/1997 |

OTHER PUBLICATIONS

Mosby—1997 7th Edition 755–756, 1205–1206.*
Derwent WPIL on Questel, week 9722, London: Derwent Publications Ltd., AN 97-237926 & EP,A1,0770384 (Montefarmco spa), abstract.

(List continued on next page.)

*Primary Examiner*—Thurman K. Page
*Assistant Examiner*—Blessing Fubara
(74) *Attorney, Agent, or Firm*—Smith, Gambrell & Russell, LLP (57) ABSTRACT

Mucoadhesive antimicrobial complexes of polycarbophil, i.e. a cross-linked polyacrylic acid with bioadhesive properties, and an imidazole or triazole derivative with antifungal or antiprotozoal activity, in its basic form, for use in the topical treatment of mucosal affections. The complexes are obtainable by dissolving each of the two starting products in a common solvent, then joining together the two solutions in relative amounts such as to contain the same number of equivalents of the two starting products, evaporating the solvent and then drying and, if required, pulverizing and sieving the product so obtained. Particularly preferred are formulations in gel in propylene glycol comprising an econazole-polycarbophil or omoconazole-polycarbophil complex, with an excess of polycarbophil, together with pharmaceutically acceptable carrier and excipient substances, for use as sustained release antifungals for vaginal administration.

25 Claims, 6 Drawing Sheets a   econazole (base)
b   econazole - polycarbophil

OTHER PUBLICATIONS

Database WPIL on Questel, week 9635, London: Derwent Publications Ltd., AN 96–353281, & US,A,5536743 (Curatek Pharm. LP), abstract.

Database WPIL on Questel, week 9230, London: Derwent Publications Ltd., AN 92–249830 & WO, A1,92/10998 (Bombart, F.), abstract.

Database WPIL on Questel, week 9204, London: Derwent Publications Ltd., AN 92–028853, & JP,A,3–275619 (Nissui Seiyaku KK), abstract.

Database WPIL on Questel, week 9101, London: Derwent Publications Ltd., AN 91–006976 & WO,A1,90/14832 (Curatek Pharm. LP), abstract.

Database WPIL on Questel, week 8928,London: Derwent Publications Ltd., AN 89–206169 & US,A,4837378 (Curatek Pharm. Inc.), abstract.

Database WPIL on Questel, week 8423, London: Derwent Publications Ltd., AN 84–141201 & DE,A,3244027 (Bayer AG), abstract.

* cited by examiner

FIG. 1 a  clotrimazole (base)
b  clotrimazole-polycarbophil
c  metronidazole (base)
d  metronidazole-polycarbophil

FIG. 2

FIG. 3 a  omoconazole (base)

b  omoconazole-polycarbophil

□ FORMULATION A (with the omoconazole-polycarbophil complex)
◇ FORMULATION B (with omoconazole (base))

BIOADHESIVE COMPLEXES OF POLYCARBOPHIL AND AZOLE ANTIFUNGAL OR ANTIPROTOZOAL DRUGS

This application is a 371 of PCT/IT97/00187 filed Jul. 26, 1997.

The present invention concerns bioadhesive complexes of polycarbophil and azole antifungal or antiprotozoal drugs. More specifically, the invention relates to the formulation of a complex of a cross-linked polyacrylic acid having remarkable mucoadhesive properties, known with the name of polycarbophil, and an imidazole or triazole derivative having antifungal or antiprotozoal activity, in the base form, for use in the topical treatment of mucosal affections.

As it is known, the diseases of a microbial origin affecting the mucous membranes, which may be treated by exploiting the trans-mucosal administration route, are many and widespread. In particular, among the diseases of this kind which affect the urogenital system, the mycotic infections are very common, and among these, specifically, the candidiases.

Candida albicans represents the species belonging to the Candida genus which is most commonly involved in human candidiases, and is the only species pathogenic on laboratory animals. The said species is held to be responsible of most superficial mycoses (muco-cutaneous mycoses) and of some serious deep mycoses, and is commonly present on the mucous membranes surfaces, such as those of the buccal cavity and of the gastrointestinal tract in man, in equilibrium with the endemic flora of the said regions. In the healthy population equilibrium conditions are normally established between the invasive potential of the fungus and the defence mechanisms of the host, which are able to limit the tissue invasion and, possibly, to eradicate the infection from the mucous membranes surface. The onset of a pathological process is the consequence of the breach of such equilibrium, and this may be either due to the different virulence of the infecting yeast or to the reduced resistance of the host. The importance of the host defence mechanisms, both natural and acquired, against candidiases is strongly confirmed by the incidence of fungal infections, and, specifically, candidiases, in immunocompromised subjects.

The candidiases of the urogenital system, much more widespread in women than in men, are characterised by itch and discharge and, upon clinical examination, by erythema, edema and, sometimes, ulcerous or papular lesions. Epidemiologic statistics on the incidence of vaginal candidiases are difficult to establish, although it may be considered that the said incidence has greatly increased in the last few years, also due to a wider use of hormone contraceptives and of antibiotic antimicrobials. Candidiases, and in general all of the fungal affections of the urogenital system, may be therapeutically treated with antimicrobial drugs for topical use, specifically imidazole derivatives such as econazole, tioconazole, miconazole and the like, or triazole derivatives such as terconazole, or also with drugs for oral administration, in particular of the triazole type, such as fluconazole. It is usually recommended to initially use the topical azole therapy, to be replaced by a systemic therapy in non responsive patients or in patients who do not withstand the topical therapy. This is due to the slight toxicity of the agents for systemic administration in comparison with agents which perform their activity in situ, as well as to the need to limit the use of these drugs in order to avoid the occurrence of resistant strains.

Among the antifungal drugs mentioned above, econazole, i.e. 1-{2-[(4-chlorophenyl)methoxy]-2-(2,4-dichlorophenyl)ethyl}-1H-imidazole, is particularly widespread and extensively tested. It has been synthesised by Godefroi et al. in 1969 (J. Med. Chem., 12, 1969, 784, and U.S. Pat. No. 3,717,655). The antimicrobial activity of econazole, which has been extensively shown in vitro, is exerted against a wide variety of fungi and against some gram-positive bacteria, while no activity on gram-negative bacteria is present. The main site of the antimicrobial action is represented by the cellular membrane system, similarly to what happens for the other imidazole antifungal agents. In vitro tests with *Trichophyton rubrum, Saccharomyces cerevisiae,* and *Candida albicans* have shown an increase in the permeability of the cell covering exposed to econazole. Said increase occurs both in the growing and in the grown-up cells, thus showing that the antimicrobial activity is due to an action on the formed membranes, and not to the formation of defective membranes in the growth phase. The main action of the drug is the inhibition of 14-α-demethylase, a cytochrome $P_{450}$-dependent microsomial enzyme system important for the synthesis of sterols. The said action has two effects: it causes a build-up of 14-α-methylsterols, and compromises the synthesis of ergosterol, which is necessary to the cytoplasm membrane. The built-up methylsterols may desegregate the close packing of the phospholipids acyl chains, thus compromising the functions of some enzyme systems connected to the membrane.

Econazole is used mainly for topical administration in the treatment of vaginal dermatomycoses and candidiases. Several medicinal products containing econazole as the active ingredient are present on the market, specially for vaginal administration. In most of the said medicinal products econazole is not present as the base, but in the form of its nitrate salt.

Another kind of microbial diseases which have been treated with therapies based on azole active ingredients, to be administered normally through the trans-mucosal route, are the infections caused by protozoa of the genus Tnchomonas. These infections generally occur in women, as cervicites, vaginites and vulvovaginites, which may also be associated with candidiases or with other bacterial infections. The active ingredient of choice for trichomoniases is metronidazole, which also belongs to the group of imidazole derivatives. For the topical treatment of infections caused by Trichomonas, both in the man and in the woman, metronidazole is advantageously combined with an imidazole derivative having mainly an antifungal action, i.e. clotrimazole.

The conventional administration forms used for the topical antimicrobials of the kinds referred to above are most commonly creams, suppositories for vaginal administration (pessaries, inserts, ovules) and tablets. In the case of econazole, for instance, there are commercially available pessaries and creams based on econazole nitrate, which represent the preparations of choice, as well as douches (lavages) and foams for external use, both in the nitrate and in the base form, which are generally used as adjuvants in the therapy. Pessaries (containing from 50 to 150 mg of active ingredient) and creams (with 1% by weight of active ingredient, to be applied in 5 g doses) are administered once a day, preferably just before going to bed in order to improve retention. The said forms do not allow, in general, to obtain an optimal bioavailability of the drug. Actually, for the therapy to perform at best its action it is necessary that the following conditions are realised: a) a good adhesion of the medicament on the infected site, and b) the complete release of the active ingredient. Very often the above does not occur with the medicinal products now in use: in the case of the suppositories for vaginal administration, in particular, the problem of retention arises, since as soon as the fusion has occurred the preparation may be rapidly discharged from the site of administration.

A suitable spreading of the formulation on the infected site, if possible followed by an interaction with the mucous layer of the said site, could result in a remarkable increase of the bioavailability of the drug. The said result may be achieved by increasing the duration and the closeness of the contact between medicament and mucous membrane: on these grounds the concept of bioadhesion, and in particular mucoadhesion, has recently gained a remarkable importance in the formulation of systems for the controlled release of drugs for trans-mucosal administration, including, but not exclusively, the systems for vaginal topical administration.

By the term bioadhesion it is meant the creation of an intimate contact, for a prolonged period of time, between a pharmaceutical material and a biological substrate, due to the formation of chemical bonds, to interfacial forces and/or to simple physical interactions between the two surfaces. When the bioadhesive interaction is established between the pharmaceutical material and the mucus which covers most of the tissues, the phenomenon is referred to as mucoadhesion. The advantages obtainable by administering an active ingredient through a bioadhesive pharmaceutical form are manifold, and may be synthesised in the following points:

localisation of the drug in a specific region: this is advantageous in a topical therapy, since the increase in the duration and in the closeness of the contact between pharmaceutical form and tissue improves the bioavailability of the drug;

increase of the in situ residence time: the pharmaceutical form has a prolonged activity, and this allows to reduce the number of daily administrations, thus improving the patient's compliance;

optimal contact with the absorption surface: this results in a better drug permeation through the tissues, inhibits the degradative enzyme activity on the active ingredient and reduces the mucus secretion;

maintenance of a high concentration gradient between the pharmaceutical form and the absorption site: this allows an optimal release of the drug, in accordance with the known laws describing the passive diffusion.

In the last years a great interest has been shown for the inclusion of bioadhesive polymers in conventional pharmaceutical forms. The so obtained bioadhesive forms mainly consist of polymer materials which are capable of interacting with mucus or with mucins. The features that a bioadhesive polymer should show in order to be pharmaceutically acceptable may be summarised as follows:

absence of toxicity;

ability to form a strong non-covalent bond with the epithelial cells of the mucous surfaces, and to quickly adhere to the moist surfaces;

ability to incorporate the drug readily and in a repeatable way, without exerting any adverse effect on the release thereof.

A number of bioadhesive polymers may be employed, in particular, in vaginal preparations: among the natural hydrogels one may cite starch, collagen, gelatin, some dextrans and also cellulose derivatives, including hydroxypropylmethylcellulose, hydroxypropylcellulose and sodium carboxymethylcellulose. Among the synthetic polymers capable of forming hydrogels only two classes appear to be employed in preparations for vaginal administration: polyethylene oxides (high molecular weight ethylene glycols) and polyacrylic acids.

Among the latter, a particularly advantageous product in view of its bioadhesive properties is polycarbophil (produced by B.F. Goodrich Company of Cleveland, Ohio, under the trade name Noveon® AA-1). Polycarbophil is an acrylic acid polymer loosely cross-linked with divinyl glycol, in particular with a quantity comprised between 0.5 and 1% by weight of 3,4-dihydroxy-1,5-hexadiene, corresponding to CAS No. 9003-01-04. The particles making out polycarbophil are swellable, but not soluble, in water, and they swell to different extents also in organic solvents, in strong mineral acids and in bases, while remaining insoluble. The water swelling features depend both on pH and on the ionic strength of the solution: the swelling degree increases with increasing pH. The amount of water that the polymer may absorb ranges from 15–35 ml per gram, at low pH values (1–3), to 100 ml per gram, in neutral or basic medium. Polycarbophil is described, together with other polymers of a similar chemical nature, in the U.S. Pat. No. 3,202,577 (R. L. Markus, 1965), where it is proposed for use in the treatment of diarrhoea, in view of its outstanding ability of swelling and absorbing liquids.

Later, it has been found that polycarbophil shows excellent mucoadhesive properties, which have been extensively described in the literature (see, e.g., H. Park and R. Robinson, J. Controlled Release, 2, 1985, 47–57; K. V. R. Rao and P. Buri, Int. J. Pharm., 52, 1989, 265–270). The polymer interaction with mucin is made easier by the fact that the polymer chains undergo swelling in water, and this allows a good degree of interpenetration with the glycoprotein chains of mucus present on the tissues surface.

The mucoadhesive properties mentioned above are actually the core of the European patent publications No. 0 163 696 and No. 0 501 523, in the name of Columbia Laboratories Inc., concerning the use of a class of polymer products, including polycarbophil as the preferred example, as bioadhesives for the production of sustained release pharmaceutical products. In the said documents (the second one of which is a divisional application of the first one) the bioadhesive polymeric product is proposed for use in admixture with pharmaceutical or cosmetic active ingredients, but it has also been proposed, by the same research group, to use polycarbophil alone, for the treatment of various ophthalmic, vaginal and buccal affections, which are characterised by a feeling of excessive dryness of the mucous membranes. In this connection, a product for vaginal rehydration containing polycarbophil has recently been placed on the market, under the trade name Replens® Said product is said to be able to adhere to the mucosa, while gradually releasing, for about 72 hours, its water content (S. H. Leung and J. R. Robinson, Polym. News, 15, 1990, 333–342).

The European patent No. 0 497 956 discloses sustained release formulations similar to the foregoing ones, but based on the calcium salt of polycarbophil, wherein the active ingredient to be delivered is incorporated in the polymeric matrix formed by calcium polycarbophil through dissolution or dispersion of the active ingredient in the matrix. As an alternative, a hydrogel matrix of calcium polycarbophil may be formed, by adding water to the formulation. The interaction of the polymeric matrix with the active ingredient results in an intimate mixture, through which the active ingredient slowly diffuses and from which it is said to be released in a controlled way.

On the basis of the above known art, it appears that the features of polycarbophil could be advantageously exploited for the production of mucoadhesive mixtures with azole antifungal and/or antiprotozoal drugs for transmucosal administration, in particular for vaginal topical use. With the object of obtaining sustained release bioadhesive products wherein the adhesion of the drug to the mucous membrane to be treated is even higher, thus resulting in a further increase of the above-mentioned advantages brought about by the use of a bioadhesive excipient, the present invention proposes to realise a true complexation between polycarbophil and the azole active ingredient, in its base form. The foregoing results in a new chemical entity wherein the drug is tightly bound to the bioadhesive agent, rather than in a physical mixture between drug and mucoadhesive carrier.

The foregoing is made possible by the chemical nature of the chosen bioadhesive polymer, having reactive carboxyl groups, and of the azole active ingredients, which, when not salified, are of a basic nature. When contacted with each other in suitable reaction conditions, the compounds form complexes which not only benefit from the bioadhesive properties of polycarbophil, but also show a release of the active ingredient extremely prolonged in time and characterised by a uniform rate. In practice, the resulting formulations are capable of: a) adhering to the mucosa as a result of the action of the polymer component, and b) releasing the azole derivative in situ very slowly and with a constant rate.

The administration of azole-polycarbophil complexes shows, when compared with the administration of the corresponding free base or of a salt thereof (e.g., the nitrate), all of the advantages already mentioned with reference to the bioadhesive systems. But also in comparison with the administration of a simple physical mixture of polycarbophil and active ingredient, as it will be clear further on, superior characteristics are obtained as concerns the duration and the uniformity of the delivery, in addition to, obviously, a more intimate and durable contact between the active ingredient and the mucosal surface. The increase of the in situ residence time, together with the type of release of the drug from the complex, result in a prolonged action, thus affording a reduction of the number of daily administrations and an improvement of the patients' compliance. In addition, the closeness of the contact between the complex and the mucous membrane may allow a higher amount and rate of permeation of the drug through the tissues, while reducing the degradative enzymatic activity on the active ingredient.

Therefore, the present invention specifically provides a mucoadhesive antimicrobial complex of polycarbophil, i.e. a cross-linked polyacrylic acid with bioadhesive properties, and an azole derivative with antifungal or antiprotozoal activity, in its basic form.

In particular, the said azole derivative may be an imidazole derivative, chosen from the group consisting of: econazole, clotrimazole, metronidazole, tioconazole, fenticonazole, isoconazole, ketoconazole, sulconazole, bifonazole, omoconazole, azanidazole, butoconazole and oxiconazole. Particularly preferred for use in the complexes of the invention are econazole, clotrimazole, omoconazole and metronidazole, the first three having antifungal activity, and the fourth one having anti-trichomonas activity.

As an alternative, the azole derivative may be a triazole derivative, such as fluconazole, terconazole and itraconazole. Said compounds show the same antifungal spectrum and the same mechanism of action as antifungal imidazole derivatives, but some of them, differently from imidazoles, may also be administered systemically. In all cases, owing to their chemical nature, the complexation mechanism of triazoles with polycarbophil is similar to that of imidazoles.

The mucoadhesive antimicrobial complexes according to the invention may be obtained, in general, by dissolving each of the two starting products in a common solvent or mixture of solvents, or in two different solvents compatible with each other, then joining together the two solutions in relative amounts such as to contain the same number of equivalents of the starting products, and subsequently evaporating the solvent. Preferably, the solid product obtained from the evaporation is dried, pulverised and sieved. The amount of polycarbophil required is previously calculated by measuring the neutralisation equivalent thereof by potentiometric titration. In the experimentation carried out in the frame of the present invention, the said value turned out to be equal to about 7 meq/g.

According to some preferred embodiments of the invention, the econazole-polycarbophil, clotrimazole-polycarbophil, omoconazole-polycarbophil and metronidazole-polycarbophil complexes are obtained each by preparing two solutions in methanol, one containing the drug in its basic form and the other containing the polymer, the relative amounts of drug and polymer to be dissolved having been calculated in such a way as to obtain in the two solutions an equal number of equivalents of reactant. For polycarbophil the neutralisation equivalent has been evaluated by potentiometric titration carried out with 0.01 N NaOH on 100 mg of polymer, and the result obtained, as pointed out before, is about 7 meq/g. The methanol solutions are mixed together and the resulting solution is placed in an evaporator at 40° C. The solid product so obtained is subsequently dried under vacuum at 50° C., then pulverised and sieved.

The bioadhesive complexes according to the invention can be used for the production of sustained release antifungal and/or antiprotozoal pharmaceutical products, by incorporating them into suitable formulations together with pharmaceutically acceptable vehicles and excipients. In order to further increase the bioadhesivity of the product, in addition to the complex as such an excess amount of non-complexed polycarbophil may be present. Said excess amount may be of use for adjusting the viscosity and the consistency of the product.

The compositions containing the compounds according to the invention, with a suitable choice of the excipients, may be in any one of the known pharmaceutical forms used for products to be administered by the transmucosal route. For the production of antifungal and/or antiprotozoal medicaments for vaginal administration the gel form is particularly preferred. In the said form the complex according to the invention, if desired together with an excess of polycarbophil, and with other conventional formulation ingredients such as, e.g., preservatives and thickening agents, are formulated in a gel of propylene glycol and/or polyethylene glycol.

By way of example only, some gel compositions containing the complexes of the invention, suitable for vaginal topic administration, are described below.

EXAMPLES OF GEL COMPOSITIONS FOR VAGINAL ADMINISTRATION

| formulation 1 | econazole (base) (in the complex) | 3.00 g |
| --- | --- | --- |
| | polycarbophil | 2.12 g |
| | (of which 1.12 g complexed with econazole) | |
| | methyl-paraben | 0.20 g |
| | propyl-paraben | 0.02 g |
| | propylene glycol | q.s. to 100.0 g |
| formulation 2 | econazole (base) (in the complex) | 2.00 g |
| | polycarbophil | 1.75 g |
| | (of which 0.75 g complexed with econazole) | |
| | hydroxypropylcellulose | 2.00 g |
| | methyl-paraben | 0.20 g |
| | propyl-paraben | 0.02 g |
| | propylene glycol | q.s. to 100.0 g |
| formulation 3 | omoconazole (base) (in the complex) | 3.00 g |
| | polycarbophil | 2.01 g |
| | (of which 1.01 g complexed with omoconazole) | |
| | hydroxypropylmethylcellulose | 1.50 g |
| | methyl-paraben | 0.20 g |
| | propyl-paraben | 0.02 g |
| | polyethylene glycol 200 | 50.0 g |
| | propylene glycol | q.s. to 100.0 g |
| formulation 4 | chlortrimazole (base) (in the complex) | 1.00 g |
| | polycarbophil | 1.41 g |
| | (of which 0.41 g complexed with clotrimazole) | |
| | hydroxypropylmethylcellulose | 1.50 g |
| | methyl-paraben | 0.20 g |
| | propyl-paraben | 0.02 g |
| | polyethylene glycol 200 | 50.0 g |
| | propylene glycol | q.s. to 100.0 g |
| formulation 5 | metronidazole (base) (in the complex) | 3.00 g |
| | polycarbophil (in the complex) | 2.50 g |
| | pectin | 3.00 g |
| | methyl-paraben | 0.20 g |
| | propyl-paraben | 0.02 g |
| | propylene glycol | q.s. to 100.0 g |

BRIEF DESCRIPTION OF THE DRAWINGS

Some experimental results showing the characteristics of the bioadhesive antimicrobial complexes and their performance as sustained release therapeutic agents are given below, together with some graphs shown in the accompanying drawings, wherein.

BIOADHESION TESTS OF NON-COMPLEXED POLYCARBOPHIL

In a preliminary study carried out in the frame of the research which led to the present invention, the mucoadhesive properties of polycarbophil and of other reference polymers were evaluated by measuring the force required to separate two surfaces coated with mucin (25 wt. % dispersion of pig gastric mucin absorbed on filter paper) between which a matrix obtained by direct compression of the polymer under test was interposed. The reference polymers used are Carbopol® 940 (water-soluble polymer of acrylic acid cross-linked with polyalkenyl polyethers, produced by B.F. Goodrich), pectin, xanthan gum, hydroxypropylcellulose (HPC), polyvinyl alcohol (PVA) and hydroxypropylmethylcellulose (HPMC).

The apparatus used for the measurements consisted in a microbalance to which there was attached, below the pan and by means of a nylon thread, a cylindrical body A weighing 8.2 g. One of the two mucous surfaces was connected to the body A, while the other was fixed to a second cylindrical body B, of the same diameter of the body A. The polymer product under test, once applied on the mucous surface fixed to the body A, was contacted with the mucous layer applied to the body B. The whole assembly was placed, with the body A on the upper side and below the scale, in a double-walled beaker placed in thermostat at 37° C., resting upon a mobile platform. After maintaining the contact between the two mucous layers and the polymer for one minute, the platform was lowered at a constant speed (i.e. 2.5 mm/min), thus causing the breaking of the bioadhesive binding between the polymer surface and the mucous surface. Before being applied on the mucin surfaces the polymer matrixes were hydrated for 5 minutes in distilled water. The electric motor of the platform and the balance were connected with a computerised system for the data acquisition and processing.

The force required to separate the polymer surface from the mucous layer was recorded as a function of the distance between the two surfaces, and from the plots so obtained the area under the curve was calculated, the latter representing the adhesion work. The data processing was carried out by means of a KaleidaGraph software (from Synergy Software). The results of the adhesion tests for the different materials tested, expressed in terms of adhesion work per surface unit, are reported in the following table.

TABLE 1

Measurement of bioadhesion

| Polymer | Adhesion work per surface unit (erg/cm$^2$ ± s.e.) |
| --- | --- |
| Carbopol ® 940 | 1070.00 ± 69.00 |
| pectin | 160.52 ± 8.92 |
| polycarbophil | 1083.20 ± 95.06 |
| xanthan gum | 555.53 ± 35.48 |
| hydroxypropylcellulose | 306.00 ± 42.12 |
| polyvinyl alcohol | 346.70 ± 40.80 |
| hydroxypropylmethylcellulose | 767.02 ± 49.12 |

From the above values it is evident that the acrylic polymers Carbopol® 940 and (to an even greater extent) polycarbophil show a much stronger mucoadhesion than that offered by the other polymers tested.

Characterisation of the Azole-polycarbophil Complexes

Econazole-polycarbophil, clotrimazole-polycarbophil, metronidazole-polycarbophil and omoconazole-polycarbophil complexes, produced according to the preferred method described above, underwent differential scanning calorimetry (DSC) tests, and their behaviour was compared with that of the corresponding bases. In the analysis, exactly weighed samples of the materials were heated at the rate of 5 kcal/min in suitable temperature ranges comprised between 50 and 190° C.

Figure 1:
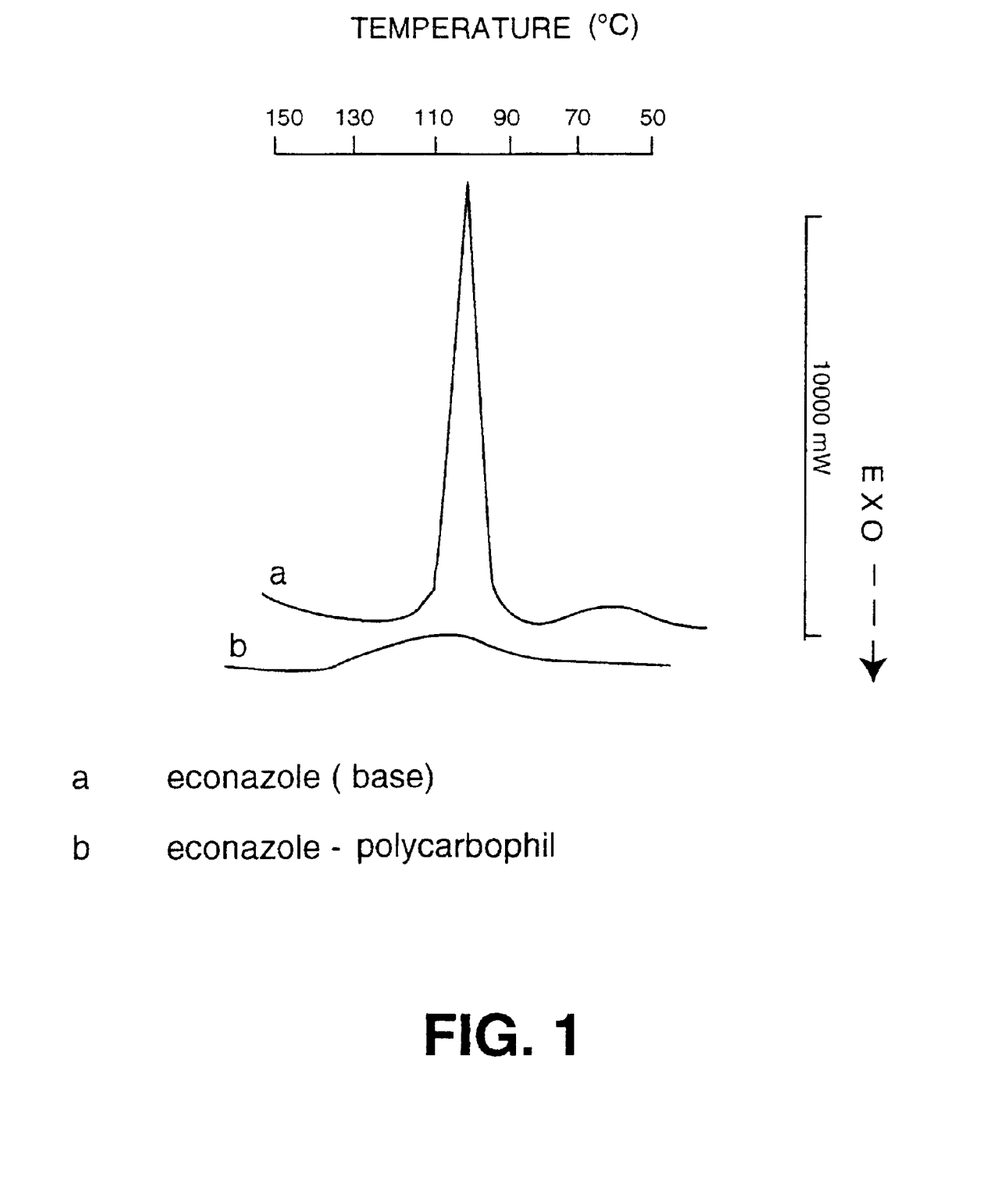
FIG. 1 shows, in comparison with each other, the thermograms obtained by differential scanning calorimetry (DSC) of econazole (base) and of the econazole-polycarbophil complex according to the invention.

The thermograms so obtained with econazole (base) and with the corresponding complex are shown in FIG. 1: as it may be observed, the formation of the complex is confirmed by the fact that in the corresponding thermogram (curve b) the endothermic fusion peak of econazole (curve a) has completely disappeared.

Figure 2:
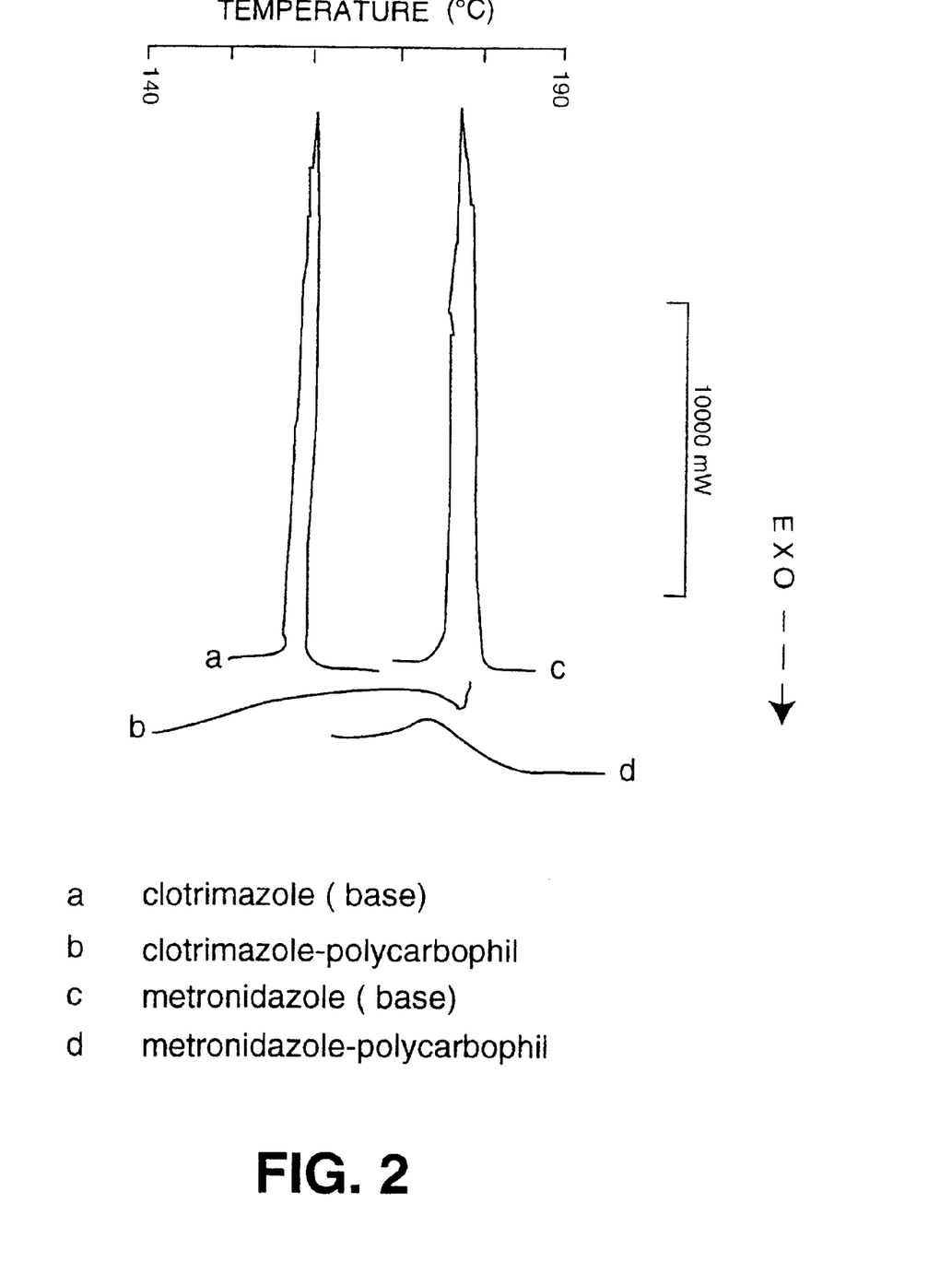
FIG. 2 shows the thermograms obtained by DSC of clotrimazole (base) and of metronidazole (base) and, in comparison with them, the thermograms of the clotrimazole-polycarbophil complex and of the metronidazole-polycarbophil complex.
Figure 3:
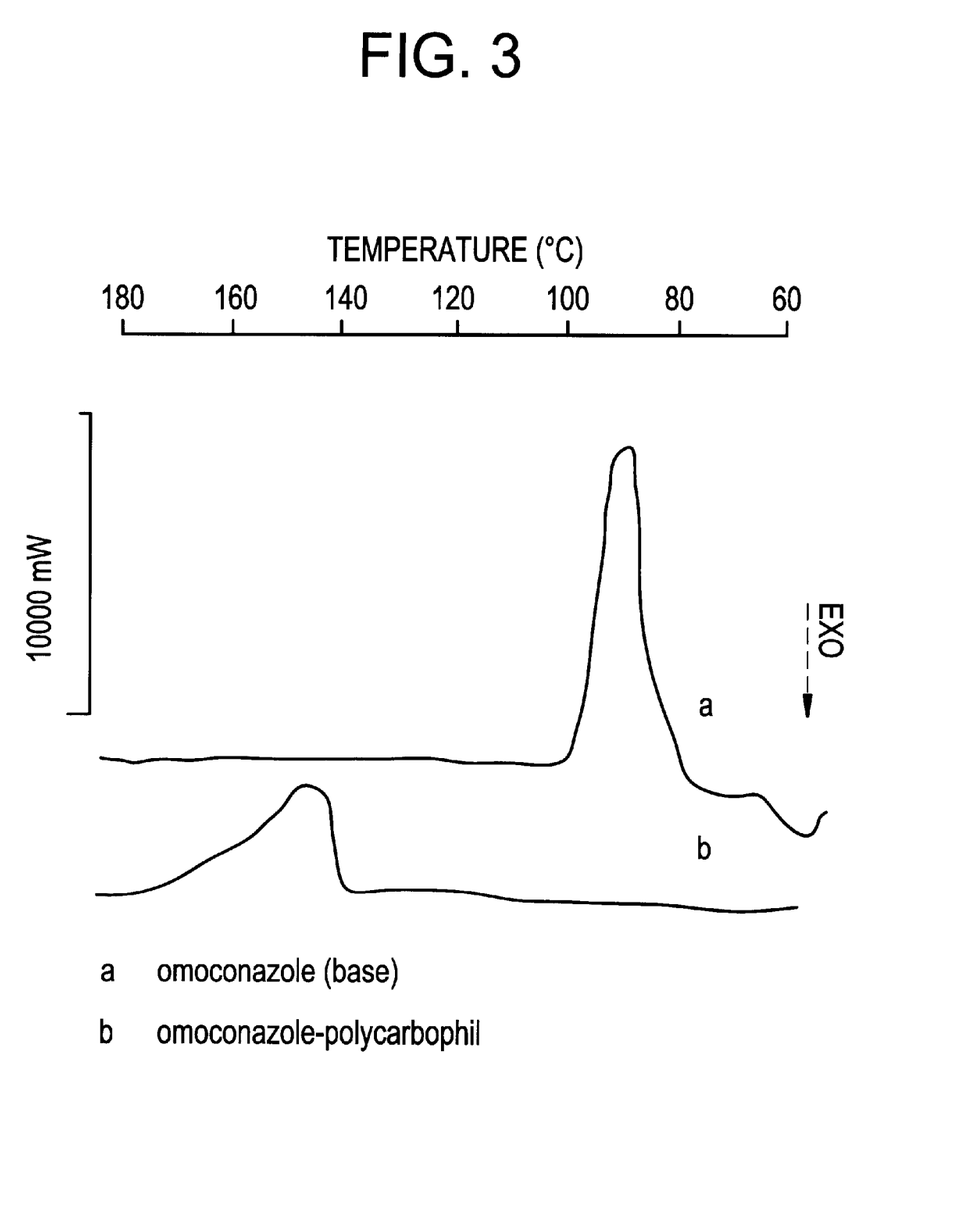
FIG. 3 shows, in comparison with each other, the thermograms obtained by DSC of omoconazole (base) and of the omoconazole-polycarbophil complex.

Similarly, in FIGS. 2 and 3 there may be observed that in the thermograms of the complexes clotrimazole-polycarbophil (curve b of FIG. 2), metronidazole-polycarbophil (curve d of FIG. 2) and omoconazole-polycarbophil (curve b of FIG. 3) the endothermic fusion peaks of the corresponding non-complexed bases (respectively, clotrimazole, curve a of FIG. 2, metronidazole, curve c of FIG. 2 and omoconazole, curve a of FIG. 3) have completely disappeared.

In vitro Release Tests

Release of the drug from the complex and comparison with a physical mixture

The release studies on econazole were carried out by applying the continuous flow method described in the Italian Pharmacopoeia, IX ed. The continuous flow apparatus consists of a cylindrical cell wherein the sample of powder under test is placed, of a reservoir for the solvent medium and of a peristaltic pump which feeds the cell with the said medium. The working section of the cell is a 30 mm high cylinder, having an inner diameter of 22.6 mm, closed at the top of by a fiberglass filter, which prevents undissolved particles from leaving the cell. The lower section, of a conical shape and provided with a hole (1 mm diameter) allowing the flow of the solvent medium, is filled-up with glass beads (3 mm diameter). The latter allow a uniform distribution of the solvent medium on the whole cross-section of the cell. Stirring is provided by the solvent circulation, from the bottom upwards. The solvent is constantly fresh, as the cell operates in open circuit.

An exactly weighed amount (i.e. 300 mg) of the econazole-polycarbophil complex was placed in the cell, at the centre of the stainless steel support provided therein. The solvent medium (i.e. lactic acid at pH 4.5), kept in thermostat at 37° C., is introduced into the cell by means of the perstaltic pump at a flow rate of 3.0 ml/min. The drug concentration in the receiving phase is determined by means of a spectrophotometer, continuously performing absorbance readings ($\lambda$=272 nm).

Figure 4:
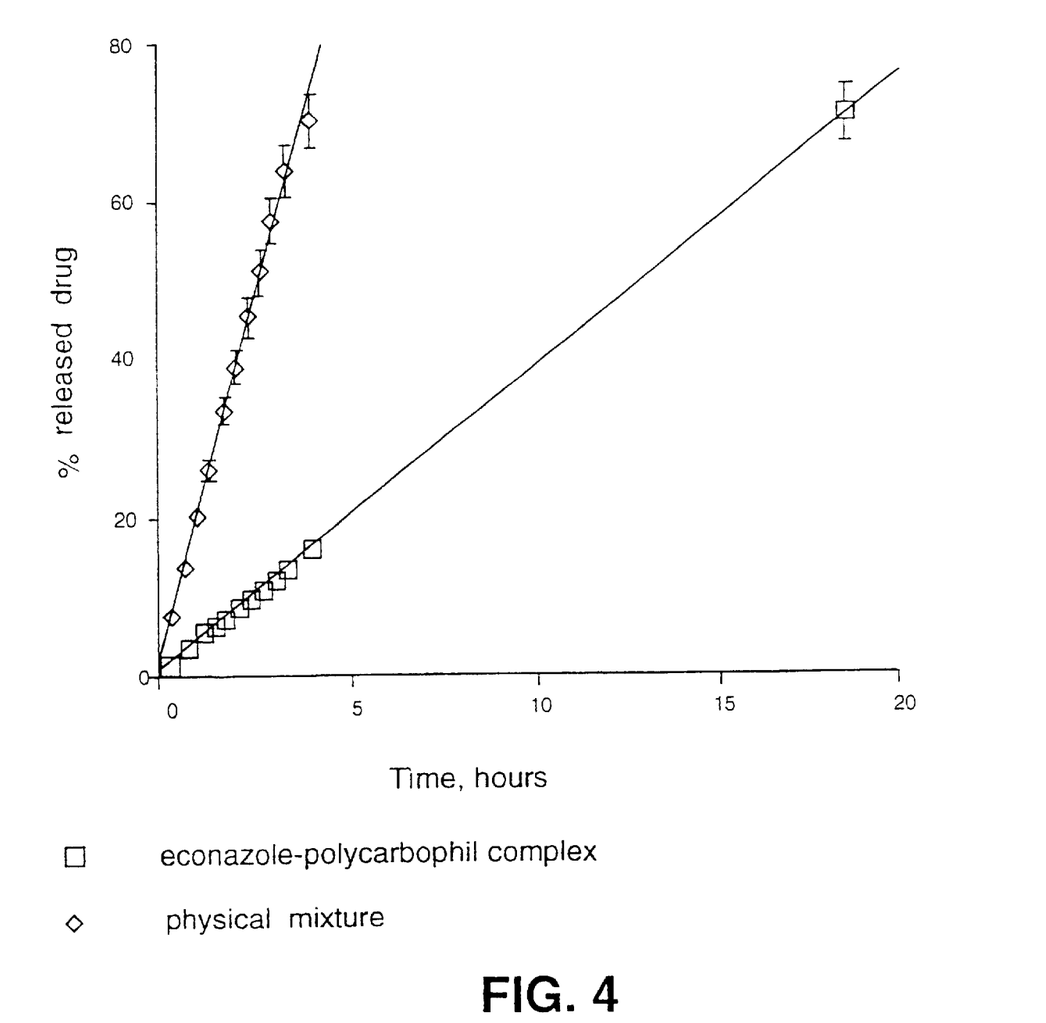
FIG. 4 shows, in comparison with each other, the release profiles of econazole from the complex according to the invention and from a physical mixture of polycarbophil and econazole.

The results of a comparison test between the complex according to the invention and a physical mixture of econazole and polycarbophil are shown in FIG. 4. In the latter, the release profile of the drug from the complex is marked by the reference sign □, while the release profile of the drug from the physical mixture is marked by the reference sign ◇. It may be observed that in both cases there is a linear relationship between the amount of drug released and time (y=3.792x+0.901, with r=1.000 for the complex and Y=17.907x+2.488, with r=0.997 for the physical mixture). Therefore, the drug is released at a constant rate from both powders. Significantly different is, on the other hand, the value of the release rate, as the econazole-polycarbophil complex releases the drug much more slowly than does the physical mixture. In practice, 70% of the active ingredient is released from the complex in 18.5 hours, while the same amount is released from the physical mixture in 4 hours.

Obviously, the slow release of econazole from the complex is an advantageous feature, as in the in vivo administration it results in a prolonged pharmaceutical activity.

Release of the drug from gel formulations

Further tests were carried out for evaluating the release of econazole and of omoconazole from gel formulations wherein the active ingredient was contained either in the form of a complex with polycarbophil or as the non-complexed base. The said tests were carried out with a Gummer type vertical diffusion cell, with a diffusional area of 2.3 cm$^2$ and a receiving compartment having a capacity of 11.0 ml. The cell was equipped with a thermostat set at 36±0.5° C. The receiving phase was made out of a buffer at pH 4.5, stirred at a constant speed of 600 r.p.m. An exactly weighed amount (i.e. 1 g) of gel was placed in the donor compartment, in contact with a Spectrapore dialysis membrane, used as the support.

The drug content of the receiving phase, sampled at suitable time intervals and filtered, was determined spectrophotometrically ($\lambda$=272 nm).

The release tests referred to in the following concern two couples of formulations, one couple containing econazole and the other containing omoconazole. In each couple one formulation contains the complex imidazole-polycarbophil according to the invention (formulation A) and the other contains the corresponding noncomplexed base, to which hydroxypropylcellulose was added as bioadhesive ingredient (formulation B). Specifically, the two couples of formulations tested had the following compositions:

| | Econazole | |
|---|---|---|
| formulation A | econazole (base) (in the complex) | 3.00 g |
| | polycarbophil | 2.12 g |
| | (of which 1.12 g complexed with econazole) | |
| | propylene glycol | |
| formulation B | econazole (base) | 3.00 g |
| | hydroxypropylcellulose | 2.12 g |
| | propylene glycol | q.s. to 100.0 g |
| | Omoconazole | |
| formulation A | omoconazole (base) (in the complex) | 3.00 g |
| | polycarbophil | 2.01 g |
| | (of which 1.01 g complexed with omoconazole) | |
| | propylene glycol | q.s. to 100.0 g |
| formulation B | omoconazole (base) | 3.00 g |
| | hydroxypropylcellulose | 2.01 g |
| | propylene glycol | q.s. to 100.0 g |

Figure 5:
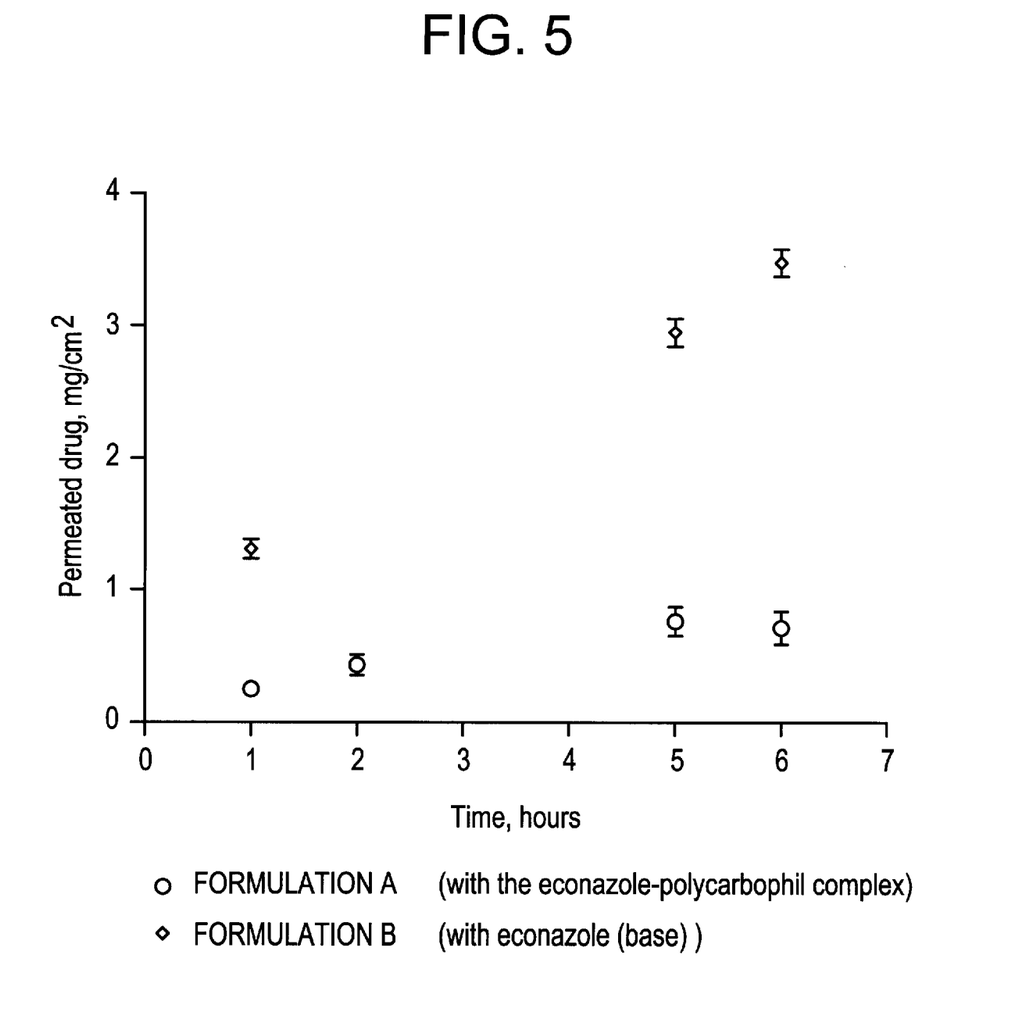
FIG. 5 shows, in comparison with each other, the release profiles of econazole from two pharmaceutical compositions in gel, one with the econazole-polycarbophil complex and the other with econazole (base)
Figure 6:
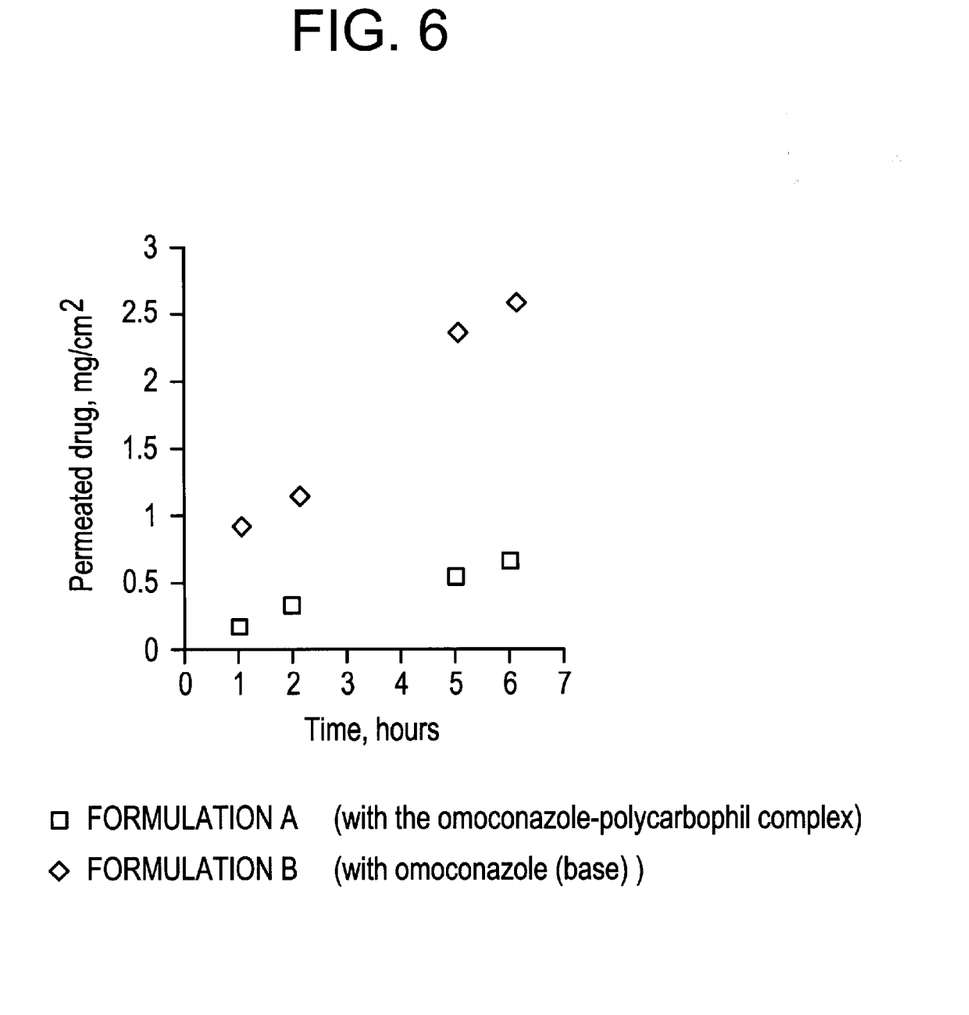
FIG. 6 shows, in comparison with each other, the release profiles of omoconazole from two pharmaceutical compositions in gel. one with the omoconazole-polycarbophil complex and the other with omoconazole (base).

The tests results are respectively shown in FIG. 5 (econazole) and in FIG. 6 (omoconazole). In FIG. 5 the release profile of the drug from the Formulation A is marked by the reference sign ○, while in FIG. 6 the corresponding release profile is marked with the reference sign □. In both figures the release profile of the same drug from the Formulation B is marked by the reference sign ◊. Both in the case of econazole and in the case of omoconazole it is evident that the drug is released much more slowly from the formulation according to the invention, wherein it is complexed with polycarbophil, than from the comparison formulation.

Microbiological Activity—In vitro Tests

The experimental activity referred to below was aimed at testing the activity of the econazole-polycarbophil complex on different strains of *Candida albicans,* while ascertaining, as a first step, the ability of the econazole-polycarbophil complex of fully releasing the active ingredient. A further object was to compare the activity of the complex with that of the drug alone. The sensitivity of the micro-organism to the antifungal-bioadhesive combination was evaluated by means of antifungal assays carried out in liquid or in solid medium.

Two standard American Type Culture Collection (ATCC) strains were used for the assays, i.e. those deposited under the numbers ATCC 48867 and ATCC 23866. Econazole (base) and the econazole-polycarbophil complex were prepared by using different concentrations of the active ingredient depending on the assay requirements, as well as different solvents (i.e. propylene glycol, DMSO), with or without a thickening excipient substance (i.e. hydroxypropylcellulose). The activity of each solvent was also tested, as well as the activity of the excipient and that of polycarbophil alone.

Antifungal assay in solid medium

The antifungal activity has been evaluated in an assay in solid medium using Petri dishes containing Sabouraud medium with 2% agar. The dishes were uniformly seeded, with the aid of a sterile pad, with an aqueous suspension containing *C. albicans* at a density of 2 McFarland. By means of an instrument of 6 mm diameter, incisions were made on the dishes in order to obtain regular cavities in the agar thickness. Each one of the substances under test was placed in one of these cavities, in amounts ranging from 50 to 100 $\mu$l. The plates were then incubated for 24 h in a thermostat at 37° C. The antifungal activity was evaluated by measuring the diameter of the inhibition of *C. albicans* growth around each cavity.

The antifungal assay in solid medium turned out to be a highly sensitive and reproducible assay also for the products under test. At least five separate experiments for evaluating the inhibition halos were carried our for each one of the two different strains and for each one of the compounds examined. Similar results were obtained with each compound in all of the experiments performed. The results obtained for the two strains of *C. albicans* tested were always comparable, thus showing the similar susceptibility of the two strains to the tested compounds.

Table 2 shows the results of the tests carried out with the ATCC 48867 strain. Polycarbophil alone showed no inhibition activity on the growth of the two *C. albicans* strains. The econazole-polycarbophil complex (EC-PC) and econazole alone showed a similar inhibition activity, which has been evaluated at different concentrations, with or without hydroxypropylcellulose (HPC).

TABLE 2

Antifungal assay in solid medium

| Compound | | Diameter of inhibition halo (mm) | |
|---|---|---|---|
| | Concentration (%) | Preparation with HPC | Preparation without HPC |
| polycarbophil | 1 | — | 0 |
| HPC | 1 | — | 0 |
| econazole (base) | $3 \times 10^{-2}$ | 31.2 ± 0.84 | 31.2 ± 0.84 |
| EC-PC | $3 \times 10^{-2}$ | 31.4 ± 0.55 | 31.2 ± 0.45 |
| econazole (base) | $3 \times 10^{-3}$ | 29.4 ± 0.89 | 28.6 ± 0.55 |
| EC-PC | $3 \times 10^{-3}$ | 29.2 ± 0.84 | 29.0 ± 1.22 |
| econazole (base) | $3 \times 10^{-4}$ | 20.8 ± 1.30 | 20.2 ± 1.09 |
| EC-PC | $3 \times 10^{-4}$ | 20.4 ± 1.10 | 20.8 ± 0.84 |
| econazole (base) | $3 \times 10^{-5}$ | 13.0 ± 1.00 | 12.4 ± 0.58 |
| EC-PC | $3 \times 10^{-5}$ | 12.8 ± 0.84 | 13.2 ± 1.30 |

Susceptibility test in microplate (liquid medium)

Stock solutions of econazole (base) and of the econazole-polycarbophil complex were obtained by dissolving the compounds in DMSO at a concentration of 1.5 mg/ml. Two serial 10-fold dilutions in DMSO were made starting from the stock solutions, up to a concentration of 15 $\mu$g/ml. From this concentration each compound was subsequently diluted in Yeast Nitrogen Base medium, to which 0.5% glucose and 0.05% bovine albumin had been added. The mixtures were then placed, at different concentrations, in microplate wells (90 $\mu$l volume each). 10 $\mu$l of a suspension of *C. albicans* obtained by diluting by 1/10 a preparation having a turbidity of 2 McFarland were then inoculated in each well. After 48 h of incubation at 37° C. the minimal inhibitory concentration (MIC) for the fungus was read from the microplates, on the basis of the presence or the absence of turbidity at a given drug concentration.

As it is shown in the following table, the minimal inhibitory concentration for *C. albicans* turned out to be comprised, for the two substances under test, between 6.2 and 5.3 µg/ml. These values are not different from those reported in the literature for econazole, obtained with different kinds of susceptibility assays.

TABLE 3

Suspectibility test in microplate

| Compound tested | Minimal inhibitory concentration (in µg/ml of econazole) | |
| --- | --- | --- |
| | C. albicans ATCC 48867 | C. albicans ATCC 23866 |
| econazole (base) | 5.6 ± 0.3 | 5.6 ± 0.4 |
| econazole-polycarbophil | 5.7 ± 0.5 | 5.6 ± 0.3 |

As it appears from the above data, the in vitro tests did not show any inhibitory activity by the polycarbophil polymer, tested alone, on the growth of strains of *Candida albicans*. On the other hand, a complete release of the antifungal from the econazole-polycarbophil complex has been shown, allowing the active compound to fully exert its anti-candida activity, at a level which is equivalent to that of the non-complexed active ingredient.

Microbiological Activity—In vivo Tests

In the frame of the microbiological experimentation of the products of the invention, the in vivo pharmacological activity of the econazole-polycarbophil complex has also been tested, in comparison with that of econazole (base), in the treatment of an experimental intravaginal infection by *Candida albicans*, reproduced in a murine model.

Vaginal candidiasis in rodents may be induced only in pseudoestrus conditions (P. L. Fidel, M. E. Lynch, J. D. Sobel, Infection and Immunity, 61 (5), 1993, 1990). For this reason, 72 hours before vaginal inoculation, the CBA/J (H-$2^k$) mice, described as sensible to such infection (P. L. Fidel, J. L. Cutright, J. D. Sobel, Infection and Immunity, 63 (10), 1995, 4191) were treated with 0.5 mg of estradiol valerate, dissolved in sesame oil, administered by subcutaneous route. The estrogen administration was repeated weekly until completion of the study. Blastoconoids ($5 \times 10^5$) of *Candida albicans*, strain ATCC 48867, were inoculated in the vagina of mice previously treated with estrogens. After one week from the inoculation, the infection degree was evaluated by means of vaginal washing and subsequent count of the colony-forming units (CFU) on plates of Sabouraud agar, to which chloramphenicol and gentamicin had been added.

The infected animals were divided into three test groups, each one of which underwent a therapeutic treatment for five subsequent days (from day 1 to day 5). Each therapeutic treatment respectively consisted of: 1) econazole (base) (0.5 wt. % and 1 wt. %); 2) econazole-polycarbophil complex (0.5 wt. % and 1 wt. % calculated as econazole); 3) excipients (control group). In order to better evidence the therapeutic effectiveness of the new mucoadhesive delivery system (econazole-polycarbophil complex), after 4 hours from the pharmaceutical administrations a thorough vaginal wash with PBS was carried out, so as to remove the portion of drug that did not adhere to the mucous membrane.

The infection degree was checked before starting the treatment and at the end thereof (day 6). The animals were considered cured when all of the cultures were negative, sensibly improved when less that 100 colonies were found in 50 µl of PBS, improved when the number of colonies was comprised between 100 and 990 in 50 µl of PBS; for a number of colonies above 990 the treatment was considered to be ineffective. The statistical evaluation of the results was made by means of the $\chi^2$ test.

After one week from the intravaginal inoculation with *C. albicans,* about two thirds of the animals resulted to be infected. Vaginal candidiasis in estrogen-treated mice turned out to be a stable infection; actually, the treatment of the animals with the only excipients (control group) did not show any influence on the course of the infection.

The therapy carried out as described above with the econazole-polycarbophil complex appeared to be sensibly more effective than the treatment with econazole only. The vaginal wash, carried out about 4 hours after the drug administration, allowed to evidence the mucoadhesive effectiveness of the econazole-polycarbophil complex, and to emphasise the differences between the two treatments. A difference in effectiveness, even if not statistically significant (p=0.3), was already detectable between the two different preparations in a first test wherein the econazole concentration was 0.5% by weight. The results of the said test are shown in the following table.

TABLE 4

In vivo tests-0.5 wt. % econazole

| Results | Treatment | | | |
| --- | --- | --- | --- | --- |
| | EC-PC | | econazole (base) | |
| Not improved | 0 | — | 1 | 11.11% |
| Improved | 4 | 40% | 6 | 66.66% |
| Sensibly improved | 5 | 50% | 2 | 22.22% |
| Cured | 1 | 10% | 0 | — |
| Total mice | 10 | | 9 | |

Repeating the experiment with two preparations having an econazole concentration of 1% by weight, as is shown in the following table, the difference between the activities of the two formulations turned out to be statistically significant (p=0.0371).

TABLE 5

In vivo tests-1 wt. % econazole

| Results | Treatment | | | |
| --- | --- | --- | --- | --- |
| | EC-PC | | econazole (base) | |
| Not improved | 0 | — | 3 | 18.75% |
| Improved | 5 | 31.25% | 9 | 56.25% |
| Sensibly improved | 8 | 50.00% | 4 | 25.00% |
| Cured | 3 | 18.75% | 0 | — |
| Total mice | 16 | | 16 | |

In addition, it is to be noted that the treatments with econazole-polycarbophil and econazole alone are found to be even more significantly different when the number of cured animals is added to that of the sensibly cured animals in the two groups in comparison (68.75% for the animals treated with the complex according to the invention vs. 25% for those treated with econazole (base) alone; p=0.0131).

The pharmaceutical activity of the new delivery system (econazole-polycarbophil complex), when assayed in vivo, has shown a higher effectiveness in the treatment of murine vaginal candidiasis when compared to the therapy with econazole only. This is clearly to be ascribed to the fact that the complex mucoadhesive-active ingredient allows an extremely prolonged residence of the drug in the site of action, as well as a more intimate contact between the active substance and the mucous membrane. The foregoing affords, as a consequence, a more effective recovery from the infection.

What is claimed is:

1. A mucoadhesive antimicrobial complex comprising:
   polycarbophil, having bioadhesive properties;
   chemically complexed with an azole, in its basic form, having antifungal or antiprotozoal activity.

2. The complex according to claim 1, wherein the azole comprises an imidazole.

3. The complex according to claim 2, wherein the imidazole is a member selected from the group consisting of: econazole, clotrimazole, metronidazole, tioconazole, fenticonazole, isoconazole, ketoconazole, sulconazole, bifonazole, omoconazole, azanidazole, butoconazole and oxiconazole.

4. The complex according to claim 2, wherein the imidazole comprises econazole or omoconazole.

5. The complex according to claim 1, wherein the azole comprises a triazole.

6. The complex according to claim 5, wherein the triazole is a member selected from the group consisting of fluconazole, terconazole and itraconazole.

7. A mucoadhesive antimicrobial complex of:
   polycarbophil, having bioadhesive properties; and
   an azole with antifungal or antiprotozoal activity, in its basic form; the complex obtained by a process comprising:
      dissolving the polycarbophil and the azole in one of a common solvent,
      a mixture of solvents, or two different solvents compatible with each other,
      joining together the solution or solutions in relative amounts such as to contain the same number of equivalents of the polycarbophil and the azole, and
      evaporating the solvent to obtain the mucoadhesive antimicrobial complex as a solid product.

8. The complex according to claim 7, wherein the solid product obtained from the evaporation is subsequently dried, pulverised and sieved.

9. The complex according to claim 7, wherein an amount of polycarbophil required is determined by measuring a neutralisation equivalent thereof.

10. The complex according to claim 7, wherein the azole is a member selected from the group consisting of econazole, clotrimazole, omoconazole and metronidazole, and wherein the common solvent is methanol.

11. A bioadhesive antimicrobial composition comprising:
    the mucoadhesive antimicrobial complex according to claim 1; and
    at least one of a pharmaceutically acceptable carrier and an excipient substance.

12. The composition according to claim 11, further comprising an excess of non-complexed polycarbophil.

13. The composition according to claim 11 in the form of a gel.

14. The composition according to claim 11, wherein the azole comprises econazole, and wherein the composition comprises an excess of polycarbophil, in the form of a gel in propylene glycol.

15. The composition according to claim 11, wherein the azole comprises omoconazole, and wherein the composition comprises an excess of polycarbophil, in the form of a gel in propylene glycol.

16. A mucoadhesive antimicrobial complex, obtained by a process comprising:
    dissolving a) a polycarbophil having bioadhesive properties, and b) an azole, in its basic form, having antifungal or antiprotozoal activity, in one of a common solvent, a mixture of solvents, or two different solvents compatible with each other;
    joining together the solution or solutions in relative amounts so as to contain substantially the same number of equivalents of the polycarbophil and the azole ; and
    evaporating the solvent to obtain the mucoadhesive antimicrobial complex as a solid product.

17. The complex according to claim 16, wherein the solid product obtained from the evaporation is subsequently dried, pulverized and sieved.

18. The complex according to claim 16, wherein an amount of polycarbophil required is determined by measuring a neutralisation equivalent thereof.

19. The complex according to claim 16, wherein the azole is a member selected from the group consisting of econazole, clotrimazole, omoconazole and metronidazole, and wherein the common solvent is methanol.

20. A mucoadhesive antimicrobial complex exhibiting improved sustained-release properties over a simple physical mixture, the complex comprising:
    polycarbophil, having bioadhesive properties;
    chemically complexed with an azole, in its basic form, having antifungal or antiprotozoal activity.

21. The complex according to claim 20, wherein the complex comprises a true complexation of the polycarbophil and the azole , in which the azole is tightly bound to the polycarbophil.

22. The complex according to claim 20, wherein the azole is released from the complex for an extremely prolonged time characterized by a uniform rate.

23. A mucoadhesive antimicrobial complex comprising:
    polycarbophil, having bioadhesive properties; and,
    chemically complexed with the polycarbophil,
    an azole, in its basic form, having antifungal or antiprotozoal activity,
    wherein the complex exhibits improved sustained-release properties over asimple physical mixture of polycarbophil and a salt of an azole.

24. The complex according to claim 23, wherein the complex comprises a true complexation of the polycarbophil and the azole, in which the azole is tightly bound to the polycarbophil.

25. The complex according to claim 23, wherein the azole is released from the complex for an extremely prolonged time characterized by a uniform rate.

* * * * *